(12) United States Patent
Gupta et al.

(10) Patent No.: US 12,369,992 B2
(45) Date of Patent: Jul. 29, 2025

(54) SYSTEM AND METHOD FOR WIRELESSLY POWERING, SENDING AND RECEIVING INFORMATION FROM AN INSTRUMENT IN THE BODY

(71) Applicant: Washington State University, Pullman, WA (US)

(72) Inventors: Subhanshu Gupta, Pullman, WA (US); Stephen Seslar, Mukilteo, WA (US)

(73) Assignee: Washington State University, Pullman, WA (US)

( * ) Notice: Subject to any disclaimer, the term of this patent is extended or adjusted under 35 U.S.C. 154(b) by 37 days.

(21) Appl. No.: 17/996,897

(22) PCT Filed: Apr. 26, 2021

(86) PCT No.: PCT/US2021/029123
§ 371 (c)(1),
(2) Date: Oct. 21, 2022

(87) PCT Pub. No.: WO2021/217121
PCT Pub. Date: Oct. 28, 2021

(65) Prior Publication Data
US 2023/0157668 A1 May 25, 2023

Related U.S. Application Data

(60) Provisional application No. 63/015,144, filed on Apr. 24, 2020.

(51) Int. Cl.
*A61B 34/20* (2016.01)
*A61B 5/06* (2006.01)

(52) U.S. Cl.
CPC ............... *A61B 34/20* (2016.02); *A61B 5/06* (2013.01); *A61B 2034/2051* (2016.02); *A61B 2034/2063* (2016.02); *A61B 2560/0214* (2013.01)

(58) Field of Classification Search
CPC ....... A61B 34/20; A61B 5/6852; A61B 8/445; A61B 8/4483; A61B 8/4488;
(Continued)

(56) References Cited

U.S. PATENT DOCUMENTS 6,783,536 B2    8/2004  Vilsmeier
7,575,550 B1 *  8/2009  Govari ................... A61B 90/39
                                                        600/443
(Continued)

FOREIGN PATENT DOCUMENTS

DE    102007037846 A1 *  2/2009  ............... A61B 1/04

*Primary Examiner* — Angela M Hoffa
(74) *Attorney, Agent, or Firm* — WCF IP (57) ABSTRACT

The embodiments of the present invention are directed to a novel wireless powered method, apparatus and tracking system without a wired interface to a moving catheter. The implant in the patient's body on the moving catheter is energized by an external ultrasound transmitter using acoustic pressure waves. As a general mode of operation, ultrasonic waves from outside of a patient's body are received by an array of transducer elements configured about the catheter disposed in a patient's body, wherein the array of transducer elements transforms a frequency into a resultant stored energy. The resultant stored energy powers one or more transceivers via a power management arrangement and enables RF frequencies in a desired band to be output and received by external sensors. Coupled with ultrasound backscattering capabilities, the catheter provides a dual mode for accurate triangulated locations of the distal end of a moving catheter.

23 Claims, 5 Drawing Sheets

(58) Field of Classification Search
CPC .... A61B 2034/2051; A61B 2034/2063; A61B 5/06–068
See application file for complete search history.

(56) References Cited

U.S. PATENT DOCUMENTS

| | | | |
|---|---|---|---|
| 8,200,313 B1* | 6/2012 | Rambod | A61B 8/0841 |
| | | | 600/443 |
| 10,322,289 B2 | 6/2019 | Poon et al. | |
| 11,806,187 B2* | 11/2023 | Erkamp | A61B 34/20 |
| 2003/0060700 A1* | 3/2003 | Solf | A61B 8/0833 |
| | | | 600/411 |
| 2007/0197905 A1 | 8/2007 | Timinger | |
| 2019/0053854 A1* | 2/2019 | Altmann | A61B 34/20 |
| 2019/0090957 A1* | 3/2019 | De Wijs | A61B 8/0841 |
| 2019/0269368 A1* | 9/2019 | Hauck | A61B 34/71 |
| 2020/0008775 A1* | 1/2020 | Erkamp | A61B 8/4263 |
| 2020/0345427 A1 | 11/2020 | Victor | |

* cited by examiner

TDOA (Time Difference of Arrival)

Position of NodeA, NodeB, NodeC are already known.
Based on time difference signal arriving each node to estimate the position of Tag.

$d1 = c^*T1, d2 = c^*T2, d3 = c^*T3;$ $d1-d2 = c^*(T1-T2);$
$d1-d3 = c^*(T1-T3);$ $\sqrt{(x1-xa)^2 + (y1-ya)^2} - \sqrt{(x1-xc)^2 + (y1-yc)^2} = c(T1-T3)$
$\sqrt{(x1-xb)^2 + (y1-yb)^2} - \sqrt{(x1-xc)^2 + (y1-yc)^2} = c(T2-T3)$

FIG. 9

SYSTEM AND METHOD FOR WIRELESSLY POWERING, SENDING AND RECEIVING INFORMATION FROM AN INSTRUMENT IN THE BODY

CROSS-REFERENCE TO RELATED APPLICATION(S)

The present application claims under 35 U.S.C. § 119, the priority benefit of U.S. Provisional Application No. 63/015,144 filed Apr. 24, 2020. The disclosure of the foregoing application is incorporated herein by reference in its entirety.

FIELD OF THE INVENTION

The present invention relates generally to medical devices and methods, and more particularly, the embodiments of the present invention relate to a wirelessly powered system for accurately tracking a catheter, for example, in a patient's body using in combination Radio Frequency and/or Ultrasonic backscattering.

BACKGROUND OF THE INVENTION

Discussion of the Related Art

Minimally invasive catheter based endovascular and intracardiac procedures play an increasingly critical role in modern medicine and are used to treat a wide array of medical conditions encompassing the clinical fields of interventional radiology (IR), cardiology (CC) and electrophysiology (EP). The technology that facilitates these procedures must have 3 essential components: instrument tracking/navigation capabilities, the ability to retrieve diagnostic information, and the ability to deliver therapy. In the case of electrophysiology, the system must also be able to pace (electrically excite) the heart.

Since blood is opaque, the instruments and procedural environment encountered during endovascular procedures cannot be visualized directly or with light-based cameras. Thus, other forms of imaging have been developed to allow instrument tracking/navigation during these procedures. One of the most widely utilized methods of instrument and anatomy visualization is fluoroscopy/cineangiography. However, radiation-based methods typically produce a bland greyscale 2D representation of patient anatomy, compromising the physician's ability to perform tasks in spatially complex three-dimensional anatomy and prolonging the amount of training needed to become facile in performing procedures. In addition, fluoroscopy exposes patients and practitioners to ionizing radiation, which can be harmful.

Non-ionizing methods to localize and display instruments and the endovascular intracardiac space have been developed including electromagnetic-, impedance-, and ultrasound-based navigation tools. Though these non-ionizing methods have gained traction in electrophysiology, the small field of navigation and the requirement for an active (wired) instrument have precluded their adoption in the fields of interventional cardiology and radiology.

Because the fields of interventional cardiology and radiology have a multitude of different, relatively inexpensive, passive catheters, it is to be desired that any system of tracking/visualization should allow post-market adaptation of conventional passive catheters instead of, or in addition to, the creation of custom catheters specifically manufactured to integrate into the tracking/navigation system. Currently this is not possible with conventional systems.

Therefore, a need exists to provide a non-ionizing method for accurately tracking and navigating a passive (i.e., remotely powered) moving catheter within a few millimeters of resolution within a desired environment, such as but not limited to, the intracardiac and broader intravascular environment of a patient's body. Accordingly, the embodiments herein address such a need by providing for a passive flexible catheter using a combination of multiple transducers and RF localization that serves as the feedback to the ultrasound directed energy transfer. Thus, the remotely powered system functions to accurately track the distal end of a moving catheter by way of the use of at least one of: RF signals and ultrasonic backscatter. Unlike other localizing catheters, wireless power and tracking allows for deep precise tracking without a wired catheter.

SUMMARY OF THE INVENTION

In a first aspect, the embodiments are directed to a wirelessly powered system for tracking a moving catheter within a few millimeters of resolution in a patient's body, that includes an ultrasonic transceiver configured outside of a patient's body; a moving catheter disposed within a patient's body and configured with an array of transducer elements about a longitudinal axis of the moving catheter, wherein the array of transducer elements is arranged to transform a frequency received from the ultrasonic transceiver into a resultant stored energy; a module connectively coupled to the array of transducer elements, wherein the module further comprises an energy harvesting integrated circuit, a distal radio frequency (RF) transceiver and a proximal radio frequency transceiver, wherein the module utilizing the resultant stored energy as received by the energy harvesting integrated circuit provides power for the distal radio frequency transceiver and the proximal radio frequency transceiver; at least three receiving terminals configured about the patient's body, wherein the at least three receiving terminals are configured to receive at least one of one or more ultrasonic backscatter signals resultant from the ultrasonic transmitter and one or more RF frequency signals resultant from the module; and a processor configured to determine the location of the distal end of the moving catheter via triangulation of at least one of the received ultrasonic backscatter signal and the RF signals produced by the module.

In a second aspect, the embodiments are directed to a catheter configured with an array of transducer elements about a longitudinal axis of the catheter, wherein the array of transducer elements is arranged to produce a resultant stored energy; and a module connectively coupled to the array of transducer elements, wherein the module further comprises an energy harvesting integrated circuit, a distal radio frequency transceiver and a proximal radio frequency transceiver, wherein the energy harvesting integrated circuit provides power resultant from the stored energy for the distal radio frequency transceiver and the proximal radio frequency transceiver, wherein the distal radio frequency transceiver and the proximal radio frequency transceiver are configured at a distance within the module for triangular localization calibration of a moving catheter tip position.

In another aspect, the embodiments are directed to a method for tracking a moving catheter in a patient's body that includes: disposing a moving catheter within the patient's body; transmitting one or more ultrasonic waves from outside of a patient's body and directed to the patient's body while the catheter is moving; first receiving the one or more ultrasonic waves at an array of transducer elements configured about the moving catheter, wherein the array of transducer elements transforms a frequency into a resultant stored energy; powering a module coupled to the array of transducer elements, wherein the resultant stored energy powers a distal radio frequency transceiver and a proximal radio frequency transceiver; emitting an RF frequency signal output from the distal radio frequency transceiver and the proximal radio frequency transceiver; second receiving at least one or more backscattered ultrasonic waves and the RF frequency signals at a minimum of three receiving terminals; and processing the RF frequency to triangulate a location of a distal end of the moving catheter.

Accordingly, the embodiments herein provide for a novel method, catheter apparatus, and system for wirelessly (i.e., remotely) powering, sending, and receiving information for tracking a moving catheter within a few millimeters of resolution in the body, wherein the embodiments herein that also enable, but are not strictly limited to, the capability of sensing physiologic parameters and electrically stimulating an organ such as the heart.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

DETAILED DESCRIPTION OF PRACTICING THE DISCLOSURE

In the description of the invention herein, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Moreover, it is to be appreciated that the figures, as shown herein, are not necessarily drawn to scale, wherein some of the elements may be drawn merely for clarity of the invention. Also, reference numerals may be repeated among the various figures to show corresponding or analogous elements. Additionally, it will be understood that any list of such candidates or alternatives is merely illustrative, not limiting, unless implicitly or explicitly understood or stated otherwise. In addition, unless otherwise indicated, numbers expressing quantities of ingredients, constituents, reaction conditions and so forth used in the specification and claims are to be understood as being modified by the term "about."

Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

When a method or process including two or more defined steps is described herein, the defined steps can be carried out in any order or simultaneously, except where the context excludes that possibility. For example, a disclosed method including defined steps can include one or more steps carried out before the defined steps, can include one or more steps carried out after the defined steps, can include one or more steps carried out between the defined steps, or a combination thereof.

General Description

The embodiments disclosed herein are directed to an autonomous tracking system that accurately locates and transfers higher quantities of power wirelessly to deep-tissue moving catheter implants in a cost-effective manner which is useful for a variety of applications, often medical applications. Such embodiments include a catheter navigation system/apparatus that capitalizes on, for example remotely powered integrated Radio Frequency (RF) transceivers and backscatter-based energy transfer capabilities for tracking and navigating of deep-tissue implants (i.e., a moving catheter tip-based apparatus) of >5 cm up to 10 cm. The transfer power in the otherwise passive moving catheter is provided by an ultrasonic transducer placed near a desired region (e.g., the skin) and the resultant ultrasonic wave induces a power stored capacitively for embedded circuits on the tip of the flexible moving catheter inside, for example, a patient.

The remote powering of a moving catheter is accomplished through an array of transducer elements arranged to transform a frequency (1-20 MHz, often 1 MHz) into a usable DC power stored on a capacitor located on the catheter (e.g., the module). The ultrasound-based wireless transfer has proven to be the most efficient as it results in the least attenuation (~0.1 dB/cm/MHz) and also beneficially allows large energy intensities (7.2 mW/mm$^2$) to be utilized for diagnostic studies.

The stored energy provided by the array of transducers powers a module on the moving catheter, where the module has, as part of its configuration, an energy harvesting integrated circuit, a distal radio frequency transceiver, and a proximal radio frequency transceiver but the module is not limited to solely just those components. The distal radio frequency transceiver and the proximal radio frequency transceiver as powered by the stored energy thereafter can be individually clocked to communicate with receiving terminals (also described as receiving patches herein) arranged about a patient for location of the moving catheter tip (distal end) using computer/processor triangulation of the received signals (i.e., often based on signals received by at least three receiving terminals). RF signals received from the catheter transceivers undergo demodulation to baseband, amplification, low pass filtering, and then are assigned to one or more analog to digital converters (ADCs) in a pattern controlled by an analog switch matrix.

Moreover, while the RF location arrangement is one capability of the embodiments herein to provide precise and accurate tracking within a few millimeters of resolution and navigation of a moving catheter, the ultrasonic backscattering location capability, which uses time-of-arrival processor deconvolution, additionally and beneficially aids in precisely locating the moving catheter as also interpreted by the coupled computer/processor. To reiterate for the reader, the embodiments herein in combination uses RF and pressure (ultrasonic) waves for tracking and navigation of a moving catheter. To enable these capabilities, the wireless power transfer, as previously stated, serves to energize a small pressure transducer located in the catheter tip and thereafter analog pressure measurements undergo analog to digital conversion (ADC) to result in conversion to an analog sound (backscatter) or RF wave emanating from the moving catheter tip position to sensors on or near the body where the information is digitized and displayed for the user.

Specific Description

Figure 1:
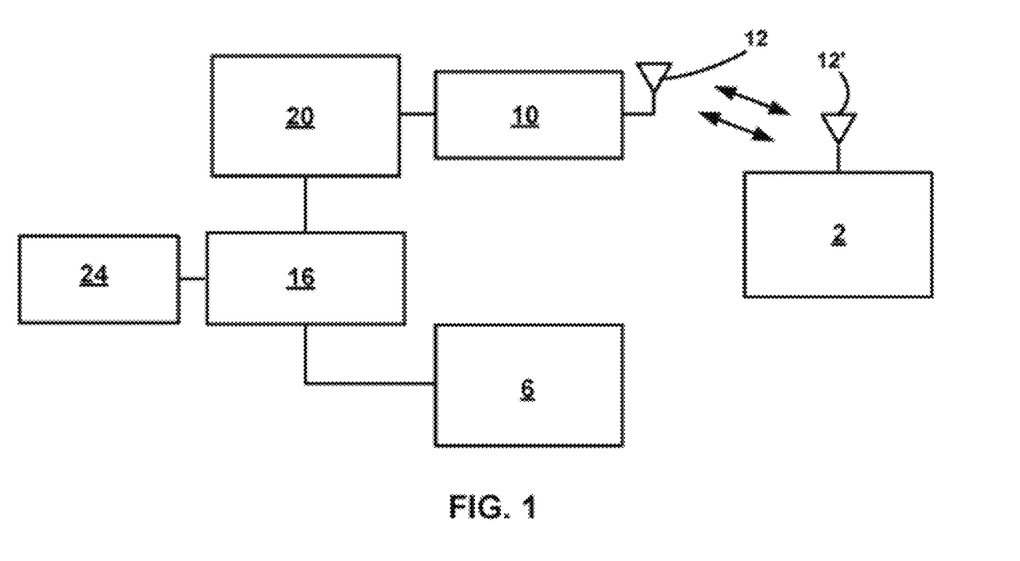
FIG. 1 illustrates an example embodiment of a wirelessly powered and localized catheter system with image processing, as disclosed herein.

Turning now to the drawings, FIG. 1 is a block diagram of a wirelessly powered and localized moving catheter system, as generally reference by the numeral 100, in accordance with embodiments of the present invention. It is to be first noted that like numerals for each figure are often utilized where common components throughout are described.

As shown in FIG. 1, the wirelessly powered and localized moving catheter system 100 includes a catheter 2 (as to be detailed in FIG. 6 infra) coupled to a catheter transmit antenna 12'. Also shown in FIG. 1 is an ultrasound generating unit (US-TX) 6 as generally understood by those skilled in the art, at least one or more sensors 10 for receiving RF signals, wherein each sensor 10 has its own a respective RF receive antenna 12, and a catheter transmit antenna 12' (RF receivers attached to 3D printed antennas) capable of communicating in a back and forth arrangement with receive antenna 12 (as denoted by the double arrows). Also shown in FIG. 1 is a computer 16, a signal processor 20 and a display 24 to provide all computational/storage and visual capabilities, etc., in tracking of the moving catheter 2.

The computer 16/processor 20 shown in FIG. 1 can include any known in the art computing device. Example computing 16 devices, as disclosed herein, often includes incorporated individual software modules, components, and the routines utilized may be a computer program, procedure, or process written as source code in C, C#, C++, Java, and/or other suitable programming languages. Image processing and data analysis often incorporated and done in MATLAB® and Origin®. The computer programs, procedures, or processes may be compiled into intermediate, object or machine code and presented for execution by any of the example suitable computing devices discussed above. Various implementations of the source, intermediate, and/or object code and associated data may be stored in one or more computer readable storage media that include read-only memory, random-access memory, magnetic disk storage media, optical storage media, flash memory devices, and/or other suitable media. A computer-readable medium, in accordance with aspects of the present invention, refers to media known and understood by those of ordinary skill in the art, which have encoded information provided in a form that can be read (i.e., scanned/sensed) by a machine/computer/processor 20 and interpreted by the machine's/computer's/processor's hardware and/or software. It is also to be appreciated that as used herein, the term "computer readable storage medium" excludes propagated signals, per se.

It is also to be noted that the wirelessly powered and localized moving catheter system, 100 can be configured with a communication interface (not shown) that includes a wireless transmitter/receiver unit to transmit signals from, for example, the processor 20 to other devices (e.g., a network, and/or via a direct connection to another device), and to receive signals from other devices and communicate the received signals back to processor 20.

The display 24 itself can include an electronic display (e.g., including a flat panel display element such as a liquid crystal display element, an organic light-emitting diode display element, an electrophoretic display element, or another type of display element) of any location coordinates and/or physiological measurements provided by the catheter 2. Moreover, such a display 24 can also include via a graphical user interface (GUI) to aid the user in orchestrating the manipulation and detection location of the catheter as well as storage of any information gathered. In addition, a GUI may be controlled remotely through the use of interconnected networks or the internet to allow for remote access of the system 100 (i.e., from another medical practitioner) from a second dispersed location if it beneficially aids in the overall procedure.

With respect to display visualization, the various embodiments enable visual context for the operator to navigate through the internal structures of the body. In some instances, the shape of the catheter 2 while the catheter 2 is moving is to be displayed by the user interface and is predetermined and is known to the system in advance by having been previously scanned and/or configured in a 3D rendering. In other environments, the catheter shape and dimensions may not be preset into the system. In this instance, in various embodiments, the system provides real-time 3D scanning of a moving catheter tip.

In one example embodiment, the scanning is performed by a commercially available scanner, such as NextEngine 3D scanner (NextEngine, Santa Monica, CA, USA). In another embodiment a custom 3D scanner is produced for quickly scanning catheter tips. In some embodiments, the 3D scans of the catheters are subsequently stored and/or catalogued in a library or database of the system (stored in computer 16, an interconnected database network, or other readable medium), such that any given catheter need only be scanned once before the catheter is preset into the system.

Figure 2A:
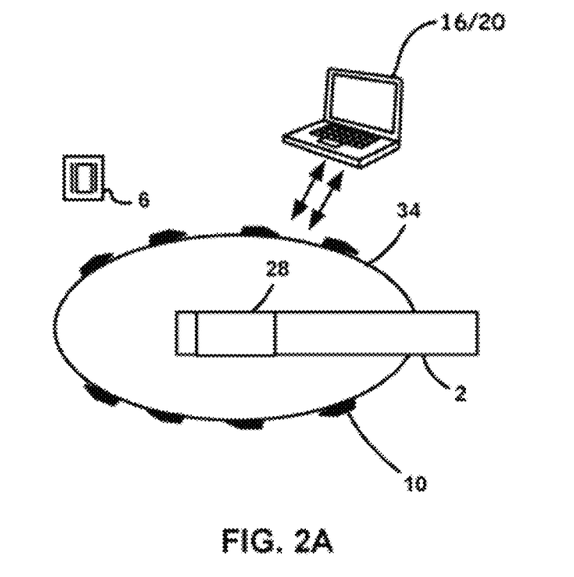
FIG. 2A shows a working arrangement of the system for locating a catheter during a procedure.

FIG. 2A shows a general graphical representation of the system 100 of FIG. 1 incorporated into a working arrangement, to include the generalized Ultrasound Transmitter (US-TX) 6, the plurality of receiving sensors 10 coupled to the computer 16/processor 20 often via a serial interface (not shown). Also shown in FIG. 2A is the novel remotely powered passive catheter 2, which can be configured as a flexible hollow-lumen catheter arranged with an electronic sensing interface (not shown) capable of angiographic applications (e.g., locate narrowing or blockages in blood vessels, measure pressure and oxygen levels, as well as capturing other physiological markers such as pressure, and respiratory activity. The sensed information will modulate the RF carrier at a few kHz which will hence be demodulated and read by the external signal processor.

The remotely powered moving catheter 2 as medically disposed within a patient 34, has as part of its arrangement a wireless module 28 affixed, often adhesively affixed to the catheter 2. Such a wireless module 28 is arranged with various components to include, but not strictly limited to, i) an ultrasonic-to-DC energy converter (see FIG. 7, U2 and AC-DC Conv) for converting the received ultrasonic transmission to DC power using a piezoelectric crystal (see FIG. 7, U2) operating at a frequency of between 1-20 MHz, often at a frequency of 1 MHz; and ii) a RF transmitter (see FIG. 6A, 62, 63; and FIG. 7, RF TX/RX) operating in the Medical Implant Communication System (MICS) band, i.e., a low-power, short-range (2 m), high-data-rate, 401-406 MHz (the core band is 402-405 MHz) to further include a low-jitter clock source (see FIG. 7, CLK), frequency multiplier (not shown), and an edge-combining power amplifier, also not shown in FIG. 2A. In addition, other medical sensors, to include a physiological sensor may also be coupled to the module.

Figure 2B:
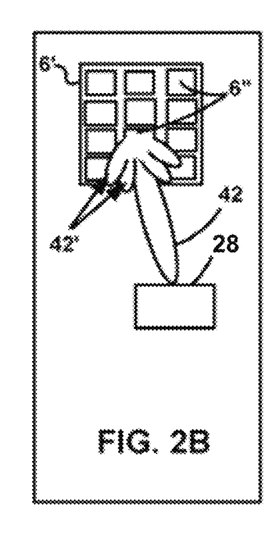
FIG. 2B shows the ultrasound generating units configured with an array of ultrasonic transducer elements providing an ultrasonic signal to the implant/module located on the catheter.

The ultrasound generating unit (US-TX) 6 generally shown in FIG. 2A can include any transmitter that can provide for sound (pressure) waves of a frequency range of at least 1 MHz and at an FDA approved power level (e.g., 7.2 mW/mm$^2$), as utilized with the embodiments herein. Often such ultrasound transmitters 6 include one or more piezoelectric elements (an array 6' of such elements as shown in FIG. 2B) sandwiched between a pair of electrodes. The electrodes of the piezo-element are connected to a voltage source, and application of voltage to the piezo-element triggers its change of dimensions at a frequency corresponding to that of the applied voltage into the media to which it is coupled, at frequencies present in the excitation pulse.

When each voltage pulse is applied, such as in an ultrasonic transmitter array 6', disclosed herein and as shown in FIG. 2B, each of the piezoelectric elements(s) 6" emits an ultrasonic wave with a central lobe 42 (again see FIG. 2B) at a primary path, such as at the moving catheter tip 70 affixed with module 28. FIG. 2B also shows undesirable side lobes 42' from each of piezoelectric elements(s) 6" that spreads out from each of the transducer elements 6" of the array 6' at angles other than the primary path, which occurs as transducer element 6" size increases. The embodiments herein thus utilize another beneficial aspect wherein the ultrasonic transmitter array 6' of the embodiments herein are configured to continuously change the transmitter power and the diameter of the array to calibrate an impedance mismatch between the input impedance of one or more piezoelectric transducers and the surrounding tissue impedance as the moving catheter propagates into deeper tissues. Such a design reduces the amplitude of side lobes 42' so as to mitigate unwanted ray paths scattering/reflecting off of anatomical features/other elements not desired to be targeted.

Backscattering

As another example beneficial embodiment, i.e., for a backscattering-based 2D Time-of Flight (TOA) design, two transducers, e.g., a transducer element 6" from the ultrasonic transmitter array 6' (see FIG. 2B) and a transducer configured in one or more sensors (patches) 10 (see FIG. 3), are arranged to operate as both a transmitter (TX) and a receiver (RX) and each engage in a burst/listen cycle (backscattering) that determines the one-way distance of the moving catheter tip from at least 3 configured sensors 10 (patches).

Such one-way distances each produce a circle of possible locations in 2D cartesian coordinates which intersect to define two possible locations, wherein a negative intersection point is discarded due to physical system constraints, leaving the positive intersection point to be obtained from Eq. 1 shown below, so as to determine an object's position (e.g., the catheter 2 tip) in each dimension.

$$x_3 = x_2 + \frac{h(y_1 - y_0)}{d}, \; y_3 = y_2 + \frac{h(x_1 - x_0)}{d}, \quad (1)$$

Another capability of the embodiments herein entails that when an ultrasonic wave e.g., 42, of the desired frequency, strikes one or more piezoelectric elements configured on a catheter 2 disclosed herein, (note that often the catheter 2 is often arranged with an array of piezoelectric elements (transducers), those element(s) produce a corresponding voltage across its electrodes, which as designed herein the present inventive embodiments, results in a wave pattern at the induced frequency. Thereafter, sensors (patches) 10 configured with circuitry to be analyzed by computer 16/processor 20 also aid in location of the moving catheter. Notably, the one or more piezoelectric elements often arranged as a circular array on a catheter 2 of the present invention provides a location not only in in x, y, z orthogonal plains but alleviates pitch, yaw, and roll deleterious effects as the catheter is maneuvered circuitously throughout a patient's body.

Figure 3:
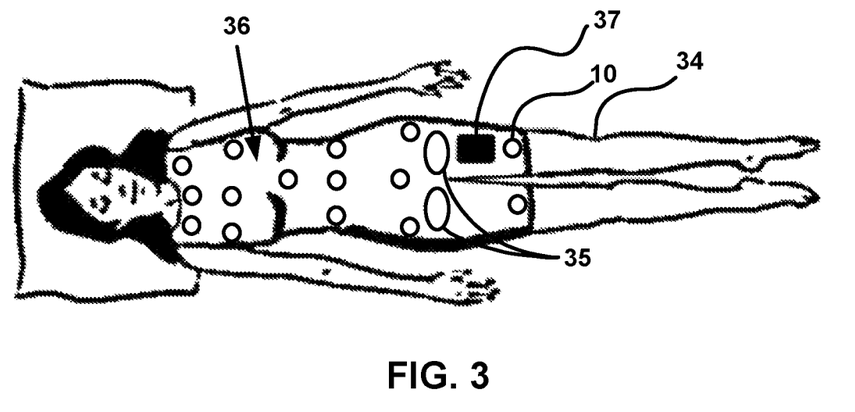
FIG. 3 is a top down view of a patient lying on a procedure table wearing a custom or commercial garment (tunic) configured with a plurality of integrated sensors (patches) to illustrate a working embodiment of the present invention.

FIG. 3 in combination with FIG. 2A shows an exemplary method of operation, wherein the catheter 2 (with the Ultrasound Transmitter (US-TX) 6 near the body) is placed into a patient 34 (also see FIG. 2), who can be arranged with a garment (a tunic) with multitude of external receivers (sensors 10 configured as patches) attached. The elliptical FIG. 35 shown in FIG. 3 are merely to illustrate openings in the tunic for catheter 2 insertion and FIG. 3 also shows an example communication module 37 arranged if desired to provide information of all of external receivers (sensors 10) to the computer 16/signal processor 20 of system 100. FIG. 3 will be understood in light of the following location methods disclosed hereinafter.

RF Triangulation

Figure 4:
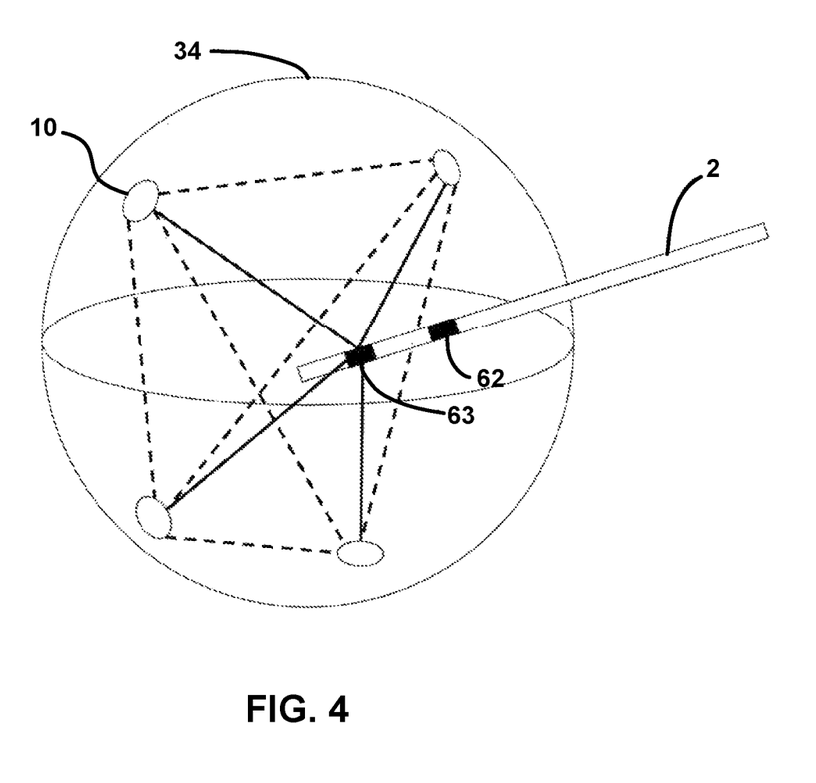
FIG. 4 is a schematic demonstrating functions of a localization system according to an embodiment.

FIG. 4 is a schematic illustration demonstrating functions of the localization system (i.e., of a localization of a moving catheter 2 tip having at least two RF transceivers 62, 63), according to an embodiment. The multitude of body sensor patches 10 are placed over a broad region of the patient's body 34 (adhesively or arranged on a custom garment (tunic)) at surface locations known to the system. The system can then be programmed to harvest data from all sensors 10 at once or dynamically and strategically select multiple three-patch combinations. Because of the broad distribution of sensor patches 10 over the patient's body 34, allows tracking of the catheter 2 while moving over a substantially broader navigation window than conventional impedance-based systems. Moreover, such a network of sensors 10 patches enables both catheter tracking and visualization as well as localization of, for example a non-limiting application, an arrhythmia source in the heart.

In each instance the location of the moving catheter in space can be solved as an inverse problem. The distance can be computed from the RF emitting electrode on the catheter to any of the sensor patches 10 in known 3D space and 3 or more patches can be used to triangulate the position of the moving catheter in space, much the same way the Global Positioning System (GPS) is able to locate the position of an object.

Thus, the catheter 2, configured with one two or more modules 28 (see FIG. 2A) is in operation medically inserted into a patient 34. Thereafter, each of the modules 28 are capable of receiving ultrasonic wireless power from Ultrasound Transmitter 6 through a piezoelectric transducer (see Ref Character 60 in FIG. 6), and a power management unit (see FIG. 7 not shown), and transferring the power to transmit a RF signal at unique frequencies, which is then tracked by the external sensor patches 10. The frequencies emitted by the transceivers (e.g., 62, 63 as detailed in FIGS. 6A and 6C) may vary depending on the clinical application but will be in the FDA approved 402-405 MHz Medical Implantable Communications band. In the setting where electrophysiologic signals are recorded by the system such as during electrophysiology procedures, the RF transmission will be modulated using conventional data modulation schemes such as frequency-shift keying (FSK), as known to those of ordinary skill in the art. The transmitted signal will thus comprise both the timestamp information for time-difference-of-arrival algorithm as well as sensed electrophysiological information demodulated by the receivers.

When a multitude of sensors 10 (patches) are distributed diffusely over a patient's 34 torso, the sensors 10 (patches) provide a substantially large area over which the moving catheter can be tracked, which is of considerable practical importance for subspecialties such as interventional radiology (IR), in which the region of procedure focus can vary considerably from procedure to procedure. The distance between the sensors 10 (patches) are dependent on the wavelength of the RF transmission as well as the depth of the module 28 having the configured two or more transceivers (e.g., 62, 63 as shown in FIG. 6). Higher frequencies allow more densely located patches (sensor receivers 10) but also suffer from larger attenuation that requires higher power transmission from the two or more transceivers (e.g., 62, 63 in FIG. 6). For higher accuracies, more sensors 10 (patches) can be utilized with the design constraint set by their wavelengths but for triangulation purposes, a minimum of three is desired.

Figure 5:
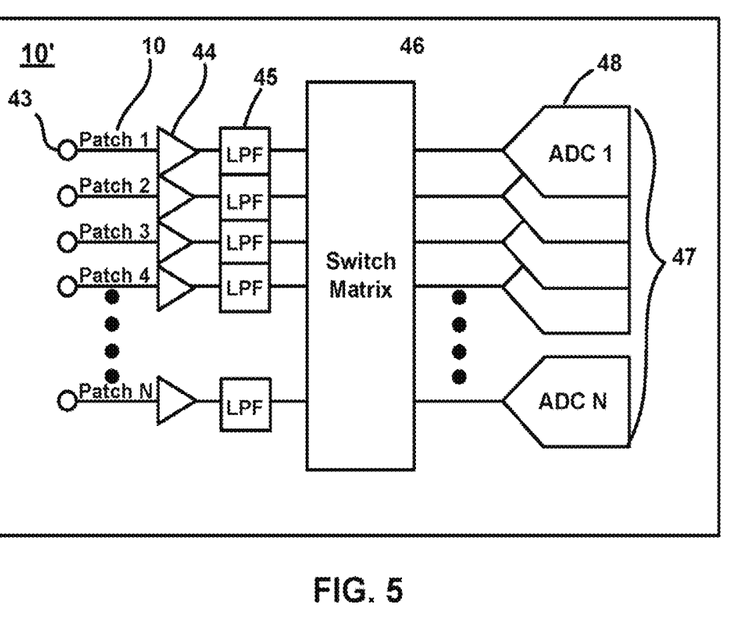
FIG. 5 is a schematic of an analog signal processing unit circuitry as utilized by the embodiments disclosed herein.

FIG. 5 shows example beneficial analog signal processing unit circuitry, denoted as 10', for each active sensor patch 10 (see shown in FIG. 3 and FIG. 4) converting the measured RF voltage signal into patch sensor 10 data. The antenna terminal 43 on sensor patch 10 receives the RF transmission indicated from the transceivers 62, 63 (see FIG. 4) arranged on module 28 affixed to catheter 2 (see FIG. 6 and description), which is then processed by the integrated radio comprising of the low-noise amplifier, mixer and an amplifier 44. In a general operation, sensor 10 patch data from each active 10 sensor patch is delivered to the processing unit circuitry 10', then filtered 45 (e.g., low pass filtered), and thereafter converted to a digital signal 47 via the ADC components 48, as shown in FIG. 5. This information is then fed to the system's computer 16 where it is used to display the catheter tip 2 in the context of internal structures of the patient. In various implementations, the visualization of the catheter tip and the internal structures facilitate the operator navigating the moving catheter and delivering therapy.

In another beneficial example embodiment, the relative position of each of the patches is derived from the same ultrasonic wireless transmission-based method, where for calibration purposes, the transmitted US signal is received on the module 28 (e.g., implant of the catheter 2). The end-of-period of the US beam transmission signals the end of power conversion and is followed by the RF transmission. The transmitted RF signal is demodulated by the external sensor patches 10 and then propagation time is communicated to the US-TX 6. In this way, the distance and relative positions between all patches is known. The distances can be calibrated using another set of electrodes on the catheter that are a known distance from one another or by having 2 or more patches on the patient that are a known distance from one another.

Figure 6A:
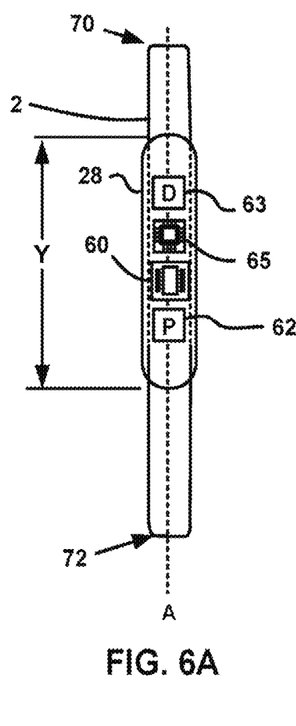
FIG. 6A shows approximate dimensions and module with general components of the catheter disclosed herein.
Figure 6B:
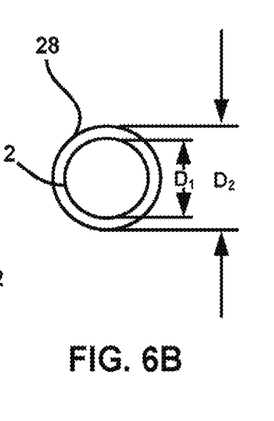
FIG. 6B shows a down the bore view of the catheter and module of the present invention.
Figure 6C:
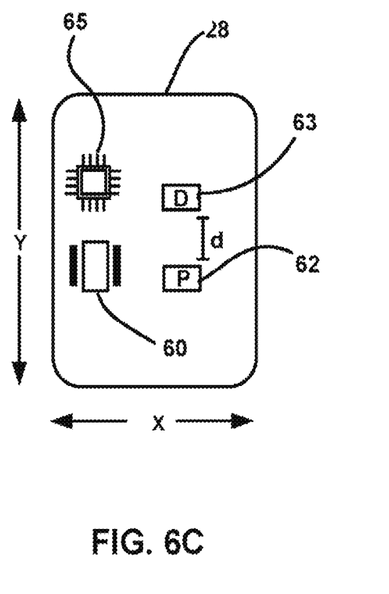
FIG. 6C shows approximate dimensions of one embodiment of a wireless current generating module according to an embodiment.

FIG. 6A, FIG. 6B, and FIG. 6C show working example configurations and example dimensions of the remotely powered moving catheter 2, often for RF signal generation, as disclosed herein. In combination, FIG. 6A, FIG. 6B, and FIG. 6C show the module 28, as described earlier, fabricated as a cylinder with an outer diameter (denoted as D2 in FIG. 6B), as shown, that depends on the outer diameter (denoted as D1 in FIG. 6B) of the catheter 2 of which can be a custom or commercially available catheter. A number of methods can be utilized to attach the module (implant) 28 to a catheter 2.

As an example embodiment, the module (implant) 28, typically often having width and length dimensions denoted as X, Y on FIG. 6C and Y on FIG. 6A, is formed as a flat, wrappable sheet a biocompatible backing adhesive (not shown). Example width X and length Y dimensions are respectively 25 mm for the length Y and 9 mm for the X dimension noting that the width largely depends on the catheter 2 diameter. Thickness for module 28 also can range but is nominally at about 0.5 mm.

In particular, FIG. 6A shows the catheter 2, with a distal end 70 (i.e., the tip) and a proximal end 72 coupled to a hub (not shown), as known and understood by those of ordinary skill in the art, of which is outside of the patient 34. Also shown are proximal 62 and distal 63 transceivers although more such receivers can be incorporated when warranted. Also generally shown is the transducer 60 that is simplistically being shown but is more often in actuality, an array of transducers 60 configured circumferentially about the diameter of the module 28 affixed to the catheter 2, a design that alleviates pitch, yaw, and roll deleterious effects as the catheter is maneuvered circuitously throughout a patient's body, as stated previously. The integrated circuit 65 in FIG. 6A and FIG. 6C generally embodies the power harvesting and management to include but is not limited to i) an ultrasonic-to-DC energy converter for converting the received ultrasonic transmission to DC power using a piezoelectric crystal operating at 1 MHz; ii) a RF transmitter operating in the MICS band comprising of a low-jitter clock source, frequency multiplier and edge-combining power amplifier.

For even more accurate localization of the moving catheter distal end 70, the system 100 of the present invention utilizes at least two or more transceivers affixed to the module 28 for calibration of provided signal information. Accurate determination of the distal tip of the moving catheter is accomplished through the calibration of the proximal and distal transceivers. First, the proximal 62 and distal transceivers 63 are localized through triangulation with patches located on the exterior of the patient. Thereafter a known distance (denoted as d in FIG. 6C, i.e., the distance between the proximal 62 and distal transceiver 63) is used to calibrate the outputs between the proximal and distal transceivers communicating with 3 or more sensors (patches) 10. The computer 16 based system receiving such often-wired patch sensor 10 data then deconvolves the information and calibrates the received signals to provide a more accurate determination of the distal end 70 of the catheter 2 while moving the catheter within the patient 34.

Accordingly, the module 28, often with the adhesive backing is affixed to the catheter 2 (e.g., a passive hollow-lumen angiographic catheter 2, by wrapping the adhesive around the shaft of the catheter 2, as visualized of the module (implant) 28 viewed down the longitudinal axis (denoted as A in FIG. 6A) to provide the final arrangement shown in side view in FIG. 6A. A measuring template (not shown) can be used to ensure placement of the module (implant) 28 is at a consistent distance from the distal end 70 of the catheter 2 tip.

Ultrasound Transfer

Figure 7:
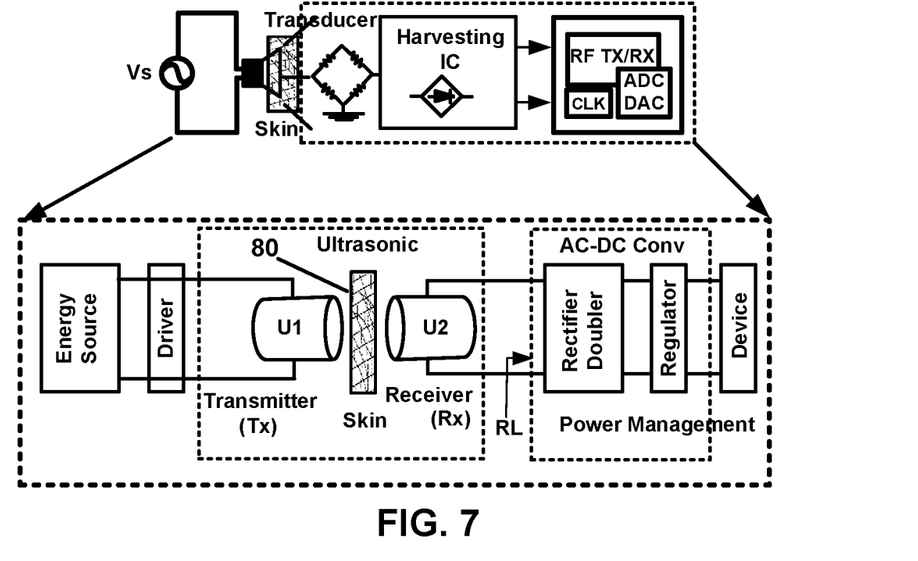
FIG. 7 shows a basic structure of an ultrasonic power transfer system for a bio-medical implant disclosed herein.
Figure 8:
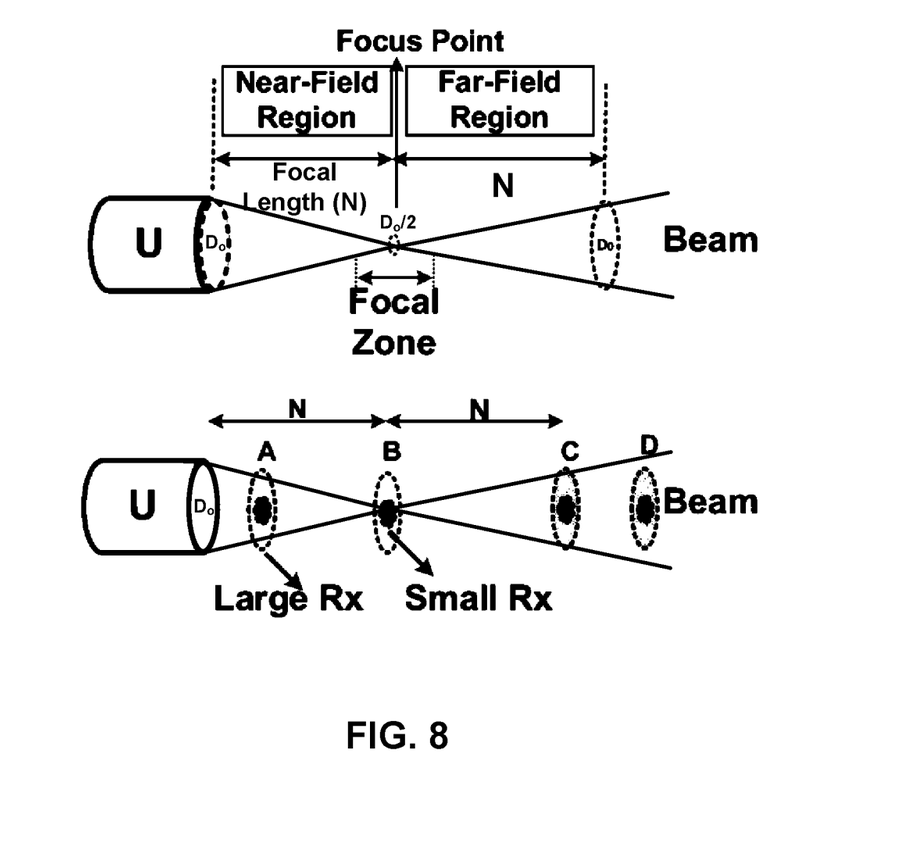
FIG. 8 shows characteristics of a generated pressure field in a medium changing with distance from a transmitter resulting in near-field and far-field patterns.

The basic structure of an ultrasonic power transfer system for a bio-medical implant is shown in FIG. 7. In this specific example, an external ultrasonic transmitter denoted as U1 converts electrical energy into a pressure wave (denoted as ultrasonic) that is transferred through the body tissue 80. The pressure wave is captured by the miniaturized device at the distal end of the catheter (D) 70 (see FIG. 6A) and transformed into a usable energy stored on a capacitor (not shown) inside the mm-sized implant (module 28). It is noted that the characteristics of the generated pressure field in a medium change with distance from the transmitter and is split into near-field and far-fields as shown in the inset in FIG. 8. At a certain distance (i.e., a Rayleigh distance) the acoustic pressure beam begins to diverge. Beyond this field, there is a decay in the intensity of the pressure field. Given the intensity of the acoustic beam is maximum at Rayleigh distance, it is often desired that the energy transducing module 28 (often in mm dimensions) with the piezoelectric transducer now denoted as U2 will be placed within the Rayleigh distance to achieve the maximum power conversion efficiencies to be converted into usable power (note power management in dashed box of FIG. 7) and thus capable of transmitting localized information as discussed above. In a specific example of an embodiment of the present disclosure, the received ultrasound beam on the module is transformed into a usable DC power stored on a capacitor for localization.

The acoustic impedances are calculated in units of Rayl where 1 rayl=1 Pa·s/m=kg/s/m2. Consequently, a larger vibration amplitude often is generated by the external transmitter to push the desired acoustic power to desired levels. In the state-of-the-art, the piezoelectric impedance is matched to the tissue impedance by inserting a single or multi-layer material with thickness off λ\4. The acoustic pressure wave propagation yields peak pressure at multiple locations that can be calculated as shown by Eq. 2:

$$X_{max}(m)=(D^2-\lambda(2m+1)^2)/(4\lambda(2m+1)), \quad (2)$$

where m is a positive integer, λ is the wavelength and D is the diameter of the transmitter array. Varying the wavelength and the diameter of the transmitter, different peak pressure locations are established over the implants trajectory and optimize the transfer of energy. Embodiments of RF wireless power transfer in the 402-405 MHz Medical Implantable Communication Band are described in this work.

Figure 9:
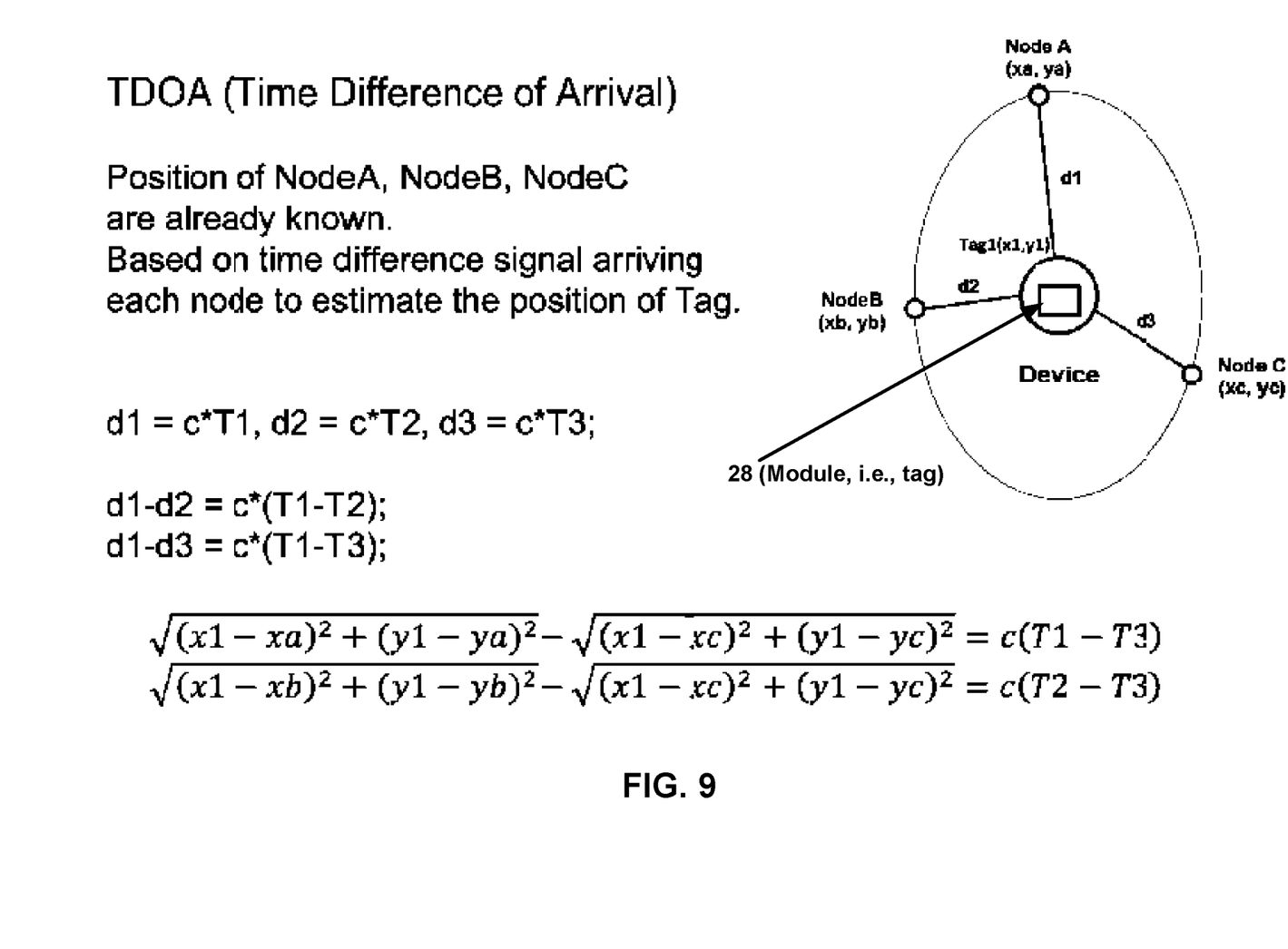
FIG. 9 shows the Localization/triangulation process utilized herein.

Embodiments to localize the implant using time-difference-of-arrival for deep-tissue floating is beneficially incorporated as previously discussed. The time-of-flight comprises of the propagation time from the external ultrasound transmission to its conversion to DC power ($t_1$), start-up time of the implant device to emitting a RF pulse ($t_2$), and finally, detection of emitted RF signal by the external patches placed on for example, a wearable garment (tunic) 36 (see FIG. 3). FIG. 9 shows the Localization/triangulation process to determine accurate positions of the module 28 (implant).

To reiterate, the RF transmission frequency band is selected in the 402-405 MHz Medical Implantable Communications (MICS) band for higher transmission distances. A multitude of body surface sensors 10 (patches (at least 3)) serve as the receivers where voltage is measured, and a distance from the patches to the sources on the catheter can be calibrated and calculated.

Wavelengths for ultrasound, as utilized herein, are comparable to millimeter-sized implants, resulting in better aperture matching and efficient energy coupling. These benefits allow for larger available power than other inductive techniques opening up new high-power applications (>100 μW) and enabling implant operation at greater depths. For these reasons ultrasonic power delivery is selected for deep-tissue medical implants.

It is also to be appreciated that the catheter is also adapted for physiology data harvesting. In such arrangements, wireless power transfer serves to energize a small pressure transducer configured on a catheter of the present invention. Analog pressure measurements undergo analog to digital conversion (ADC) and subsequent conversion to an analog sound or RF wave emanating from the catheter tip to sensors on or near the body where the information again is digitized and displayed for the user. In another example embodiment, physiological intracardiac electrogram voltages are captured by a sensor located on the tip of the catheter. These undergo ADC conversion and are again converted to an analog sound wave that is transmitted to the body to be detected on sensors at or near the skin surface where the signal is re-digitized and sent to process circuitry for amplification, filtering and display.

As known to those of ordinary skill in the art, in electrophysiology (EP) studies, there are numerous catheters involved but typically only one catheter is moved at a time. For this reason and beneficially, a two-frequency system can be utilized herein for EP applications implemented with multiple catheters. In an embodiment, a timeclock controls which electrodes emit a RF signal of a particular frequency and for what percentage of time. In this way, the roving position of the roving catheter is computed and updated more frequently, whereas the relative time allocated to emitting RF signal from (and thus updating the position of) stationary diagnostic catheters is proportionally less. In addition, to confirm that a given catheter is stationary relative to a previous interrogation, only one electrode pair needs be sampled at any given time. Should the system find that the position of the supposed stationary catheter is not static, a more thorough sampling of the catheter 2 in question can be performed and the user alerted to the change in position, if applicable.

It is also noted that the embodiments disclosed herein provides a unique non-ionizing wireless approach to catheter tracking in addition to harvesting physiological data during, for example, endovascular and intracardiac procedures, such as, but not limited to CC, IR, and EP procedures that can be easily adapted to an aftermarket passive catheter.

It is to be understood that features described with regard to the various embodiments herein may be mixed and matched in any combination without departing from the spirit and scope of the invention. Although different selected embodiments have been illustrated and described in detail, it is to be appreciated that they are exemplary, and that a variety of substitutions and alterations are possible without departing from the spirit and scope of the present invention.

We claim:

1. A wirelessly, ultrasonically powered system for tracking a catheter tip in a patient's body, comprising:
   an ultrasonic transceiver positioned outside of the patient's body and configured to generate and to direct ultrasonic pressure waves to the patient's body;
   a catheter having a distal end and configured to be disposed within and movable within the patient's body;
   an array of ultrasonic transducer elements affixed to the catheter at respective distances from the distal end and configured to receive one or more of the ultrasonic pressure waves directed to the patient's body and, in response, to
      transform the one or of the ultrasonic pressure waves into ultrasonic transducer electrical signals, and
      generate and direct ultrasonic backscatter waves to the patient's body;
   an ultrasonic-to-direct current (DC) energy harvesting integrated circuit affixed to the catheter and connectively coupled to the array of transducer elements configured to convert the ultrasonic transducer electrical signals into a DC energy and to store the DC energy as a stored DC energy;
   a distal radio frequency (RF) transceiver, affixed to the catheter at a first position with respect to the distal end, connectively coupled to the ultrasonic-to-DC energy harvesting circuit and configured to transmit, in response to receiving the stored DC energy, first RF signals;
   a proximal RF transceiver, affixed to the catheter at a second position that is a spacing distance from the first position, connectively coupled to the ultrasonic-to-DC energy harvesting circuit and configured to transmit, in response to receiving the stored DC energy, second RF signals;
   three or more ultrasound receivers located in three or more receiving terminals at positions outside the patient's body and configured to receive, as received ultrasonic backscatter signals, one or more of the ultrasonic backscatter waves from one or more of the ultrasonic transducer elements;
   three or more RF receivers located in three or more receiving terminals at positions outside the patient's body and configured to receive, as received first RF signals, one or more of the first RF signals from the distal RF transceiver and to receive, as one received second RF signals, one or more of the second RF signals from the proximal RF transceiver; and
   a processor, connected to the three or more receiving terminals and configured to determine a location of the distal end of the catheter based at least in part on triangulation of one or more of the received ultrasonic backscatter signals and triangulation of one or more of the received first RF signals and triangulation of one or more of the received second RF signals and is further based, at least in part, on the spacing distance.

2. The wirelessly, ultrasonically powered system of claim 1, wherein the three or more receiving terminals are configured as affixable or attachable to a garment worn on the patient's body and/or affixable or attachable to the patient's body.

3. The wirelessly, ultrasonically powered system of claim 1, wherein the ultrasonic transceiver is configured to generate the ultrasonic pressure waves in a frequency range of 1 MHz to 20 MHz.

4. The wirelessly, ultrasonically powered system of claim 3, wherein the ultrasonic transceiver is configured to generate the ultrasonic pressure waves in a frequency range of 1 MHz to 5 MHz.

5. The wirelessly, ultrasonically powered system of claim 1, wherein the distal end of the catheter is detectable at a depth of up to 10 cm.

6. The wirelessly, ultrasonically powered system of claim 1, wherein the system provides accuracy of the distal end of the catheter on an x-dimension and y-dimension scale having a margin of error between 4 mm to 7 mm.

7. The wirelessly, ultrasonically powered system of claim 1, wherein the system provides a localization of the distal end of the catheter to a minimum resolution of 0.3 mm.

8. The wirelessly, ultrasonically powered system of claim 1, further comprising, affixed to the catheter, a clock circuit that is configured to perform individual clocking of the distal RF transceiver and individual clocking of the proximal RF transceiver, wherein
   the proximal RF transceiver and the distal RF transceiver and the proximal RF transceiver are further configured to transmit the first RF signals and the second RF signals, respectively, at individual timings in accordance with the individual clocking.

9. The wirelessly, ultrasonically powered system of claim 1, wherein the processor is further configured to determine the location of the distal end of the catheter based at least in part on calculating a differences between respective times of arrival (TOA) of at least one of the received ultrasonic backscatter signals at different ones among at least three of the three or more ultrasonic receivers.

10. The wirelessly, ultrasonically powered system of claim 1, wherein the processor is further configured to determine the location of the distal end of the catheter based at least in part on calculating differences between respective times of arrival (TOA) of at least one of the received first RF signals at different ones among at least three of the three or more RF receivers and/or calculating differences between respective TOA of at least one of the received second RF signals at different ones among at least three of the three or more RF receivers.

11. The wirelessly, ultrasonically powered system of claim 10, wherein the differences in TOA comprises a propagation time of the ultrasonic pressure wave to the array of ultrasonic transducers the array of ultrasonic transducers, a time of conversion of the received ultrasonic pressure wave into the resultant stored DC energy, a start-up time of the distal RF transceiver to emit the first RF signals or a start-up time of the proximal RF transceiver to emit the second RF signals, and a time to detection of the one or more RF signals by the receiving terminals.

12. The wirelessly, ultrasonically powered system of claim 1, wherein the first RF signals have a first frequency and the second RF signals have a second frequency that is different from the first frequency.

13. A wirelessly, ultrasonically powered catheter system, comprising:
- a catheter, having a catheter tip, wherein the catheter is configured to be disposed within an ultrasound pressure wave conductive medium, and is further configured with an array of ultrasonic transducer elements, wherein the array of ultrasonic transducer elements is configured to generate ultrasonic transducer electrical signals in response to receiving, from the ultrasound pressure wave conductive medium, an ultrasonic pressure wave transmitted by an external ultrasound pressure wave transmitter;
- an ultrasonic-to-direct current (DC) energy harvesting circuit, supported by the catheter and connectively coupled to the array of transducer elements and configured to convert the ultrasonic transducer electrical signals to a DC energy to and to store the DC energy as a stored DC energy;
- a distal radio frequency (RF) transceiver, affixed to the catheter at a first position with respect to the catheter tip and connectively coupled to the ultrasonic-to-DC energy harvesting circuit and configured to transmit, in response to receiving the stored DC energy, first RF signals; and
- a proximal RF transceiver affixed to the catheter at a second position that is a distance from the first position and connectively coupled to the ultrasonic-to-DC energy harvesting circuit and configured to transmit, in response to receiving the stored DC energy, second RF signals.

14. The wirelessly, ultrasonically powered catheter system of claim 13, further comprising, affixed to the catheter, a clock circuit that is configured to perform individual clocking of the distal RF transceiver and individual clocking of the proximal RF transceiver, wherein
the proximal RF transceiver and the distal RF transceiver and the proximal RF transceiver are further configured to transmit the first RF signals and the second RF signals, respectively, at individual timings in accordance with the individual clocking.

15. A method for wirelessly, ultrasonically powering and tracking a catheter in a patient's body, the method comprising:
- providing the catheter as a configured catheter having a distal end and having, affixed to the catheter, an array of ultrasonic transducer elements, an ultrasonic pressure wave to direct current (DC) energy harvesting circuit connectively coupled to the array of ultrasonic transducer elements and, connectively coupled to the ultrasonic pressure wave to DC energy harvesting circuit, a distal radio frequency (RF) transceiver and a proximal RF transceiver that is positioned a spacing distance from the distal RF transceiver;
- disposing the configured catheter within the patient's body;
- moving the configured catheter within the patient's body;
- transmitting ultrasonic pressure waves from outside of the patient's body and directed into to the patient's body while the catheter is moving within the patient's body;
- receiving at the array of ultrasonic transducer elements one or more of the ultrasonic pressure waves and the array of ultrasonic transducer elements, in response, transforming the one or more of the ultrasonic pressure waves into ultrasonic transducer electrical signals, and
- generating and transmitting to the patient's body one or more backscatter ultrasonic waves;
- converting, by the ultrasonic pressure wave to DC energy harvesting circuit, the ultrasonic transducer electrical signals to a DC energy and powering, with the DC energy, a distal RF transceiver and the proximal RF transceiver;
- the distal RF transceiver, responsive to the powering by the DC energy, emitting first an RF signals signal and the proximal RF transceiver, responsive to the powering by the DC energy, emitting second RF signals;
- receiving at three or more ultrasonic receivers that are outside the patient's body and spaced apart from one another, as received backscatter ultrasonic waves, one or more of the backscatter ultrasonic waves;
- receiving, by three or more RF receivers that are outside the patient's body and spaced apart from one another, as received first RF signals, one or more of the first RF signals and one or more of the second RF signals; and
- computer processing configured to determine a location of the distal end of the catheter based on triangulation of one or more of the received ultrasonic backscatter signals and triangulation of one or more of the received first RF signals, triangulation of one or more of the received second RF signals and further based, at least in part, on the spacing distance between the proximal RF transceiver and the distal RF transceiver.

16. The method of claim 15 for wirelessly, ultrasonically powering and tracking a catheter in a patient's body, wherein the method further comprises, prior to the step of receiving the first RF signals and the second RF signals, affixing the three or more RF receivers to a garment worn on the patient's body and/or affixed to the patient's body.

17. The method of claim 15 for wirelessly, ultrasonically powering and tracking a catheter in a patient's body, wherein the ultrasonic pressure waves have a frequency in a frequency range from 1 MHz to 20 MHz.

18. The method of claim 15 for wirelessly, ultrasonically powering and tracking a catheter in a patient's body, wherein the ultrasonic pressure waves have a frequency in a frequency range of 1 MHz to 5 MHz.

19. The method of claim 15 for wirelessly, ultrasonically powering and tracking a catheter in a patient's body, wherein the step of receiving one or more of the backscatter ultrasonic waves includes detecting, based on the received ultrasonic pressure waves, the distal end of the catheter at a depth of up to 10 cm.

20. The method of claim 15 for wirelessly, ultrasonically powering and tracking a catheter in a patient's body, wherein the receiving one or more of the backscatter ultrasonic waves includes providing, based on the received backscatter ultrasonic waves, a catheter detection accuracy on an x-dimension and y-dimension scale having a margin of error between 4 mm to 7 mm.

21. The method of claim 15 for wirelessly, ultrasonically powering and tracking a catheter in a patient's body, wherein the receiving one or more of the backscatter ultrasonic waves includes providing, based on the received backscatter ultrasonic waves, a localization minimum resolution of 0.3 mm of the distal end of the catheter.

22. The method of claim 15 for wirelessly, ultrasonically powering and tracking a catheter in a patient's body, wherein the method further comprises a clock circuit individually clocking the distal RF transceiver and the proximal RF transceiver individually controllable with respect to distal RF transceiver transmitting of first RF signals and the proximal RF transceiver transmitting of second RF signals.

23. The method of claim 15 for wirelessly, ultrasonically powering and tracking a catheter in a patient's body, wherein the first RF signals have a first frequency and the second RF signals have a second frequency that is different from the first frequency.

\* \* \* \* \*